(12) United States Patent
Miracca et al.

(10) Patent No.: US 7,094,940 B2
(45) Date of Patent: Aug. 22, 2006

(54) INTEGRATED PROCESS FOR THE PREPARATION OF ALKYL AND ALKENYL SUBSTITUTED AROMATIC COMPOUNDS

(75) Inventors: Ivano Miracca, Milan (IT); Guido Capone, Milan (IT)

(73) Assignee: Snamprogetti S.p.A., San Donato Milanese (IT)

( * ) Notice: Subject to any disclaimer, the term of this patent is extended or adjusted under 35 U.S.C. 154(b) by 204 days.

(21) Appl. No.: 10/477,516

(22) PCT Filed: May 14, 2002

(86) PCT No.: PCT/EP02/05311

§ 371 (c)(1),
(2), (4) Date: Mar. 31, 2004

(87) PCT Pub. No.: WO02/096844

PCT Pub. Date: Dec. 5, 2002

(65) Prior Publication Data

US 2004/0152932 A1 Aug. 5, 2004

(30) Foreign Application Priority Data

May 25, 2001 (IT) ............................ MI2001A1110

(51) Int. Cl.
*C07C 5/333* (2006.01)
*C07C 2/64* (2006.01)
*C07C 4/02* (2006.01)

(52) U.S. Cl. ........................ 585/323; 585/319; 585/324
(58) Field of Classification Search ................ 585/323, 585/319, 324
See application file for complete search history.

(56) References Cited

U.S. PATENT DOCUMENTS 6,031,143 A 2/2000 Buonomo et al.

*Primary Examiner*—Thuan D Dang
(74) *Attorney, Agent, or Firm*—Oblon, Spivak, McClelland, Maier & Neustadt, P.C.

(57) ABSTRACT

Integrated process for the production of alkyl and alkenyl substituted aromatic compounds which comprises simultaneously dehydrogentaing in a reactor-regenerator system a mixture containing an alkyl and an aromatic alkyl hydrocarbon coming from an alkylation unit and recycling the dehydrogenated alkyl hydrocarbon thus produced, after separation, to the alkylation unit.

36 Claims, 1 Drawing Sheet

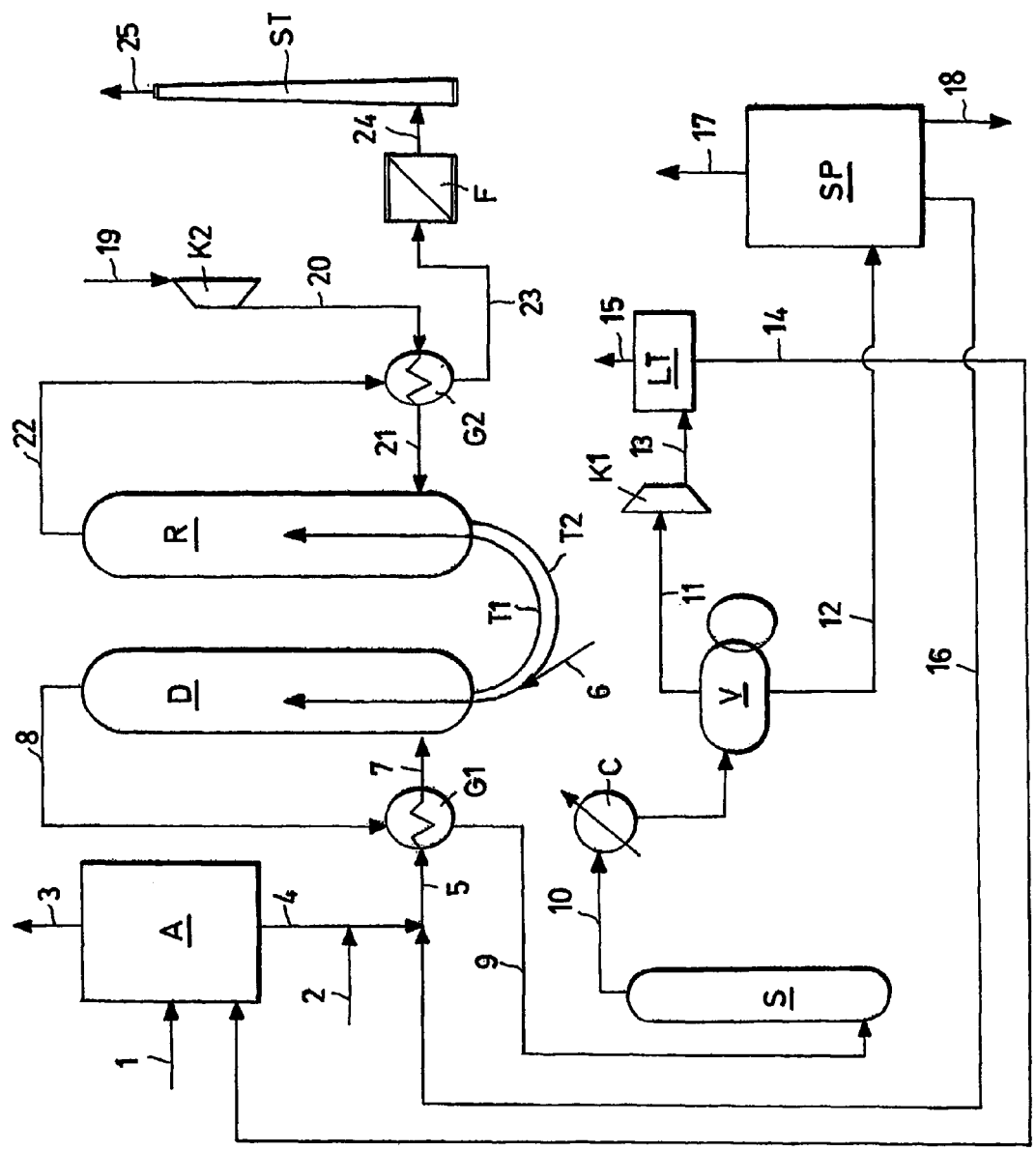

INTEGRATED PROCESS FOR THE PREPARATION OF ALKYL AND ALKENYL SUBSTITUTED AROMATIC COMPOUNDS

The present invention relates to an integrated process for the preparation of alkyl and alkenyl substituted aromatic compounds.

More specifically, the present invention relates to an integrated process for the preparation of alkyl substituted aromatic compounds, such as ethylbenzene, and alkenyl substituted aromatic compounds, such as styrene and α-methylstyrene (via cumene), from an aromatic derivative, such as benzene, and an alkane, such as ethane or propane.

Even more specifically, the present invention relates to an integrated process for the production of ethylbenzene and styrene with the contemporaneous dehydrogenation of ethylbenzene, to give styrene, and ethane, to give the ethylene necessary as reagent for the synthesis of ethylbenzene.

As is well known, styrene and α-methylstyrene are products which are used in the production of thermoplastic polymers, such as polystyrene, acrylonitrile-butadiene-styrene copolymers, styrene-acrylonitrile resins, styrene-butadiene elastomeric copolymers and in formulations for unsaturated polyester resins.

Styrene is generally prepared by the catalytic dehydrogenation of ethylbenzene by means of an adiabatic or isotherm system and in the presence of catalysts selected from metallic oxides or their mixtures, whereas ethylbenzene is prepared by the alkylation of benzene, available as a refinery product, with ethylene coming from cracking or from the dehydrogenation of ethane.

The alkylation reaction can be carried out in vapour phase, using as catalysts, zeolites with high $SiO_2/Al_2O_3$ ratios, for example ZSM-5 zeolites or Lewis acids, or in liquid phase. Details on the synthesis of ethylbenzene and on its dehydrogenation to produce styrene are provided in the Stanford Research Institute (SRI International) Reports.

The patent U.S. Pat. No. 6,031,143 describes an integrated process for the production of ethylbenzene and styrene which comprises the following operating steps:
  feeding a stream of benzene and a recycled stream containing ethylene to an alkylation unit;
  mixing the stream leaving the alkylation unit, containing ethylbenzene, with a stream consisting of ethane;
  feeding the mixture thus obtained to a dehydrogenation unit containing a catalyst capable of simultaneously dehydrogenating ethane and ethylbenzene to give ethylene and styrene respectively;
  feeding the product leaving the dehydrogenation unit to a separation section to produce a stream essentially consisting of styrene and a stream containing ethylene;
  recycling the stream containing ethylene to the alkylation unit.

The dehydrogenation unit comprises a first fluid bed dehydrogenation reactor and a second regeneration reactor of the exhausted catalyst. The latter is continuously removed from the bottom of the first reactor and is fed to the head of the second reactor where it is kept under fluid conditions by pre-heated air which flows upward. In this way the exhausted solid slowly descends downwards in countercurrent to the hot air which is rising and during this descent, it is regenerated, as the carbonaceous residues which poison it are burnt. The passage of the catalyst from one reactor to the other is guaranteed by a carrier gas such as air or nitrogen.

The contemporaneous dehydrogenation of ethane and ethylbenzene, however, creates drawbacks as these two products have characteristics which make it difficult to obtain acceptable conversions and selectivity to ethylene and styrene, under the same operating conditions. For example, to obtain a 50% equilibrium conversion of ethylbenzene to styrene at atmospheric pressure, it is necessary to operate at a temperature of about 615° C. whereas under the same conditions, the equilibrium conversion of ethane to ethylene is only about 20%. To obtain a 50% equilibrium conversion of ethane to ethylene, it would be necessary to operate at a minimum of 720° C., a temperature which would cause the thermal degradation of both the ethylbenzene and styrene. For more details, reference can be made to Paul H. Emmett "Catalysis-Hydrogenation and Dehydrogenation" vol. III, 453–471, 1995, Reinhold Publishing Corporation.

The operating conditions for embodying the process described in the U.S. patent cited above are therefore rather limited and require a particularly controlled running of the dehydrogenation reactor.

The Applicant has now found an integrated process for the production of alkyl substituted aromatic compounds, such as ethylbenzene, and alkenyl substituted aromatic compounds, such as styrene, with a greater operating flexibility and wider selection of catalyst which involves the use of a fluid bed dehydrogenation reactor in which the feeding of the alkane (ethane) is at least partially differentiated with respect to that of the ethylbenzene, as described below, exploiting the fact that in a fluid bed reactor/regenerator system with the circulation of a solid there are different temperature zones. In fact, in the fluid bed unit of the reactor/regenerator system, the heat necessary for dehydrogenation is supplied by the hot regenerated catalyst which is transferred in continuous, by means of specific transport lines, from the regenerator, operating at a higher temperature, to the dehydrogenation reactor.

The object of the present invention therefore relates to an integrated process for the production of alkyl and alkenyl substituted aromatic compounds, such as ethylbenzene and styrene, which comprises:
  a) feeding to an alkylation unit, a stream consisting of a $C_6$–$C_{12}$ aromatic hydrocarbon and a recycled stream containing a $C_2$–$C_5$ alkenyl hydrocarbon;
  b) optionally mixing the stream leaving the alkylation unit, containing the alkylaromatic compound, with a stream consisting of a $C_2$–$C_5$ alkyl hydrocarbon;
  c) feeding the stream of step (b) to a fluid bed dehydrogenation/regeneration unit containing a catalyst capable of dehydrogenating, also simultaneously, the alkyl hydrocarbon, optionally present, and the alkylaromatic compound;
  d) continuously discharging the exhausted catalyst which accumulates on the bottom of the dehydrogenation reactor and feeding it to the head of the regeneration reactor;
  e) continuously discharging the regenerated catalyst which accumulates on the bottom of the regeneration reactor and feeding it to the head of the dehydrogenation reactor;
  f) feeding the hydrocarbon stream leaving the dehydrogenation reactor to a separation section to produce a stream essentially consisting of the alkenyl substituted aromatic compound and a stream containing the alkenyl hydrocarbon;
  g) recycling the stream containing the alkenyl hydrocarbon to the alkylation unit;

said integrated process being characterized in that the fluid for transporting the catalyst, which is deposited on the bottom of the regenerator at a temperature of 650–800° C., to the dehydrogenation reactor consists of a $C_2$–$C_5$ alkyl hydrocarbon.

According to the present invention, a first stream is fed to the alkylation unit, consisting of an aromatic hydrocarbon, for example a stream of fresh refinery grade benzene charge, consequently having a purity higher than or equal to 95% by weight, and a second, recycled stream, essentially consisting of the alkenyl hydrocarbon, such as ethylene, and non-converted alkyl hydrocarbon, such as ethane. More specifically, this second stream consists of 20–95% in moles, preferably 40–85%, of ethane and 5–80% in moles, preferably 15–60% of ethylene, respectively.

In the recycled stream, 0.1–2% by weight (calculated with respect to the total ethylene+ethane weight) of other light products, for example methane and hydrogen, formed both in the alkylation phase and dehydrogenation phase, are also present.

The two streams are fed to the alkylation unit so as to have benzene/ethylene molar ratios required by current technologies, typically between 1.8 and 50, preferably between 2 and 10. The alkylation reaction is carried out with conventional systems, for example according to the method described in European patent 432,814.

Any alkylation reactor can be used in the process, object of the present invention, such as fixed bed or fluid bed reactors, carrier bed reactors and catalytic distillation reactors. For example, the catalytic distillation reactor can be used, which operates in mixed gas-liquid phase, described in U.S. Pat. No. 5,476,978 and in published international patent application WO 98/09929. In a catalytic distillation reactor, the reagents and catalytic reaction products, in the present case the reagents and alkylation reaction products, are simultaneously separated by distillation using the catalytic reactor as distillation column.

The preferred alkylation catalysts comprise synthetic and natural porous crystalline solids such as acid zeolites in which the atomic ratio silicon/aluminum ranges from 5/1 to 200/1. In particular, Y, beta zeolites, mordenite, omega, A, X and L zeolites or porous crystalline solids MCM-22, MCM-36, MCM-49, MCM 56 and ERS-10, are preferred.

In an alternative embodiment of the present invention, the alkylation reaction can be carried out using a continuous fixed bed reactor functioning in gaseous phase described, for example, in U.S. Pat. Nos. 4,409,412 and 5,517,184. In this case, the catalyst is selected from zeolites of the ZSM group in which the atomic ratio silicon/aluminum ranges from 20/1 to 200/1. Examples of ZSM-type zeolites are ZSM-5, ZSM-11, ZSM-12, ZSM-23, ZSM-35, ZSM-38 and ZSM-48 zeolites. ZSM-5 is particularly preferred.

The alkylation reaction can be carried out under temperature and pressure conditions which depend, as is well known to experts in the field, on the type of reactor and selection of reagents. In the case of the alkylation of benzene with ethylene, the reaction temperature generally ranges from 50 to 450° C. More specifically, for processes in gas phase, the temperature preferably ranges from 325 to 450° C. whereas in the case of a catalytic distillation reactor operating in mixed gas-liquid phase, the reaction temperature, varying along the catalytic bed, ranges from 140 to 350° C., preferably from 200 to 300° C.

The pressure inside the alkylation reactor is kept at values ranging from 0.5 to 6 MPa, preferably from 2 to 4.5 MPa.

The aromatic stream leaving the alkylation reactor can be treated with the conventional means to respectively obtain a substantially pure stream of non-converted aromatic product, for example benzene, a substantially pure stream of alkyl substituted aromatic compound, for example ethylbenzene, and a stream of heavier products essentially consisting of di- or polyalkyl substituted aromatic compounds, for example di- or polyethylbenzenes.

The separation system preferably consists of a series of distillation columns, from the first of which non-reacted benzene is recovered and recycled to the alkylation reactor or to a transalkylation unit as described below. Ethylbenzene is recovered from the second distillation column and fed to dehydrogenation, whereas polyethylbenzenes, such as diethylbenzenes and triethylbenzenes are recovered from the third column.

The polyalkyl substituted aromatic compounds, such as polyethylbenzenes, can be fed to a transalkylation reactor for transalkylation with $C_6$–$C_{12}$ aromatic hydrocarbons, in the case in question with benzene, to produce the corresponding monoalkyl substituted aromatic compounds, such as ethylbenzene, and increase the yield of the alkylation reaction.

The transalkylation reactor preferably consists of a fixed bed reactor functioning in liquid phase in which a conventional transalkylation catalyst is present, such as Y zeolite, beta zeolite or mordenite, preferably Y zeolite or beta zeolite. The transalkylation reaction can be carried out according to what is described in U.S. Pat. No. 5,476,978.

In the case of the transalkylation of polyethylbenzenes with benzene, the benzene/ethylene molar ratio, calculated with respect to the total moles of benzene present as such and as polyethylbenzene and with respect to the total moles of ethylene present as substituent in the polyethylbenzenes, ranges from 1.8/1 to 17/1, preferably from 2.4/1 to 10/1. The temperature in the transalkylation reactor is maintained at 50 to 300° C., preferably from 120 to 250° C., whereas the pressure is kept at 0.02 to 5.5 MPa, preferably from 0.7 to 4.5 MPa.

The $C_2$–$C_5$ alkyl hydrocarbon or, in the preferred case, ethane which can be optionally mixed with the alkylation product, is a stream of fresh charge deriving from refineries, and is therefore available, like benzene, with a purity higher than or equal to 95% by weight. The ethane fed in this phase is generally equal to 0–70% by weight of the total ethane.

The stream containing the alkylation product, optionally mixed with ethane, is fed in gas phase to the base of the dehydrogenation reactor which operates at a temperature ranging from 450 to 650° C. and at a pressure ranging from 0.1 to 3 ata, preferably at atmospheric pressure or a slightly higher value, and with a flow-rate of the reagents, expressed as hourly volumetric flow-rate of the reagents per liter of catalyst (Gas Hourly Space Velocity or GHSV) ranging from 100 to 10,000 $h^{-1}$, preferably from 100 to 1,000 $h^{-1}$, with a residence time of the catalyst in the fluid bed zone ranging from 5 to 30 minutes, preferably from 10 to 15 minutes.

To obtain an optimum dehydrogenation, the catalyst is charged into the upper part of the reactor and maintained in the fluid state by the hydrocarbon stream, fed to the base, so as to slowly descend towards the bottom in countercurrent to the gaseous phase which is rising. During this descent, the catalyst is gradually deactivated and collects on the bottom substantially exhausted.

The exhausted catalyst is continuously removed from the bottom of the hydrogenation reactor and is fed, by means of a carrier fluid, such as air or nitrogen, to the regeneration reactor. The regeneration reactor substantially operates in the same way as the dehydrogenation reactor. The exhausted solid is charged into the upper part of the reactor and is maintained in the fluid state by preheated air, optionally enriched with oxygen, so as to slowly descend towards the bottom in counter-current with the hot air which is rising. During this descent the carbonaceous residues present on the catalyst are gradually burnt so that the substantially regenerated catalyst collects on the bottom of the regenerator. Owing to the high selectivity of the dehydrogenation reactions, it is also possible to feed fuel gas to the regenerator to supply the necessary heat for completing the thermal balance of the system by its combustion.

In the regenerator, it is preferable to operate at atmospheric pressure, or slightly higher values, at a space velocity ranging from 100 to 1,000 $h^{-1}$ and with residence times of the solid ranging from 5 to 60 minutes, preferably from 20 to 40 minutes. The temperature profile inside the regeneration reactor generally ranges from 600 to 800° C.

The regenerated catalyst, at a temperature of about 650–800° C., is continuously removed from the bottom of the regeneration reactor and is fed to the dehydrogenation reactor using the $C_2$–$C_5$ alkyl hydrocarbon or ethane, as carrier fluid, in a quantity ranging from 30 to 100% by weight of the total used, preferably from 50 to 70%. During the transfer from the regenerator to the dehydrogenation reactor, the ethane is converted to ethylene, cooling the catalyst which is thus fed to the dehydrogenation reaction to create an optimum temperature profile in the reactor for the conversion of ethylbenzene to styrene.

Any catalyst capable of dehydrogenating, also simultaneously, a paraffin such as ethane and an alkylaromatic hydrocarbon such as ethylbenzene can be used in the process, object of the present invention. For example, a particularly suitable catalyst is that described in international patent application PCT/EP 00/9196 based on iron and one or more promoters, selected from alkaline or earth alkaline metals and lanthanides, on alumina in delta or theta phase or in a mixed delta+theta, theta+alpha or delta+theta+alpha phase, modified with silica, and having a surface area of preferably less than 150 $m^2/g$, determined with the BET method. More specifically, it is a catalyst which comprises:

1–60% by weight, preferably 1–20%, of iron oxide;
0.1–20% by weight, preferably 0.5–10% of at least one alkaline or earth alkaline metal oxide, for example potassium;
0–15% by weight, preferably 0.1–7% of a second promoter selected from lanthanide oxides, for example cerium, lanthanum or praseodymium;
the complement to 100 being alumina modified with 0.08–5% by weight of silica.

Further examples of catalysts are those based on gallium and platinum described in European patent 637,578 or based on chromium and tin described in European patent 894,781. Other dehydrogenation catalysts for paraffins and/or alkylaromatic hydrocarbons are described in European patents 400,448 and 335,130 and in international patent application WO 96/34843.

The catalyst based on gallium and platinum can be selected from those comprising:

0.1–34% by weight, preferably 0.2–3.8%, of $Ga_2O_3$;
1–99 ppm (by weight), preferably 3–80 ppm, of platinum;
0.05%–5% by weight, preferably 0.1–3%, of an alkaline and/or earth alkaline oxide, for example potassium;
0.08–3% by weight of silica;

the complement to 100 being alumina in delta or theta phase or in a mixture of delta+theta, theta+alpha or delta+theta+alpha phases with a surface area of less than 150 $m^2/g$, determined with the BET method.

The catalyst based on chromium and tin can be selected from those comprising:

6–30% by weight, preferably 13–25%, of $Cr_2O_3$;
0.1–3.5% by weight, preferably 0.2–2.8%, of SnO;
0.4%–3% by weight, preferably 0.5–2.5%, of an alkaline oxide, for example potassium;
0.08–3% by weight of silica;

the complement to 100 being alumina in delta or theta phase or in a mixture of delta+theta, theta+alpha or delta+theta+alpha phases with a surface area of less than 150 $m^2/g$, determined with the BET method.

At the end of the dehydrogenation, a dehydrogenated stream is recovered, essentially consisting of ethylene and styrene. More specifically, the stream comprises: 15–30% by weight of styrene; 7–15% by weight of ethylene; 10–50% by weight of non-reacted ethylbenzene and 15–55% by weight of non-reacted ethane, plus other products such as hydrogen, methane, toluene, benzene formed both during the alkylation phase and during the dehydrogenation phase.

The dehydrogenated stream is cooled, filtered and sent to a distillation section for the recovery of the styrene and non-reacted ethylbenzene, which is recycled to the dehydrogenation, and the recovery of the stream containing ethylene which is recycled, as feeding, to the alkylation unit.

If the dehydrogenation catalyst available is particularly active, i.e. low contact times of the reagent gas with the catalyst are necessary for effecting the dehydrogenation reactions, the dehydrogenation reactor can become a reactor in equicurrent, in which the solid is completely carried upwards pneumatically by the gas (riser-type reactor). In this case the superficial velocity of the gas must be higher than the terminal velocity of the largest particles present in the fluid bed. The superficial velocity of the gas phase is therefore in the order of at least a few m/s. The space velocity (GHSV) for this reactor is greater than 500 $h^{-1}$ and preferably greater than 1000 $h^{-1}$. In this case the alkyl hydrocarbon is fed to the bottom of the riser, entering into contact with the catalyst at the maximum reaction temperature. The stream containing the alkylaromatic compound is, on the other hand, injected at a suitable height along the riser when most of the dehydrogenation of the alkyl hydrocarbon has already taken place and the temperature has dropped to levels compatible with the correct dehydrogenation reaction trend of the alkylaromatic compound.

The integrated process for the production of ethylbenzene and styrene, object of the present invention, can be better understood by referring to the block scheme of the enclosed figure which represents an illustrative but non-limiting embodiment.

With reference to the scheme, (A) represents the alkylation unit, (D) the dehydrogenation reactor, (R) the regeneration unit of the catalyst, (C) a water condenser, (S) a scrubber, (SP) a separation section by means of distillations in series, (F) a filtration unit, (G1) and (G2) represent two gas-gas heat exchangers, (K1) and (K2) are compressors, (V) a gas-liquid separator, (LT) a membrane separation unit, (T1) and (T2) are the pneumatic carrier lines of the catalyst between reactor and regenerator and (ST) the stack for discharging the fumes into the atmosphere.

The present invention is therefore clearly illustrated on the basis of the enclosed scheme and previous description. In fact, a stream (1) consisting of benzene and a recycled stream (14) essentially consisting of ethylene and ethane, together with traces of hydrogen and methane, are fed, as reagents, to the alkylation unit (A). The inert products (3), which would otherwise accumulate in the production cycle, are flushed from the alkylation unit.

The alkylated stream (4), essentially consisting of ethylbenzene and ethane, is mixed to a second recycled stream (16), containing ethylbenzene, coming from the distillation section (S). A part of the ethane necessary for the integrated process, object of the present invention, can be mixed, by means of line (2), to the stream (4).

The mix (5) thus obtained, after preheating in (G1), is fed, by means of line (7), to the dehydrogenation reactor (D). The reactor (D) operates together with the catalyst regeneration unit (R). In particular, the exhausted catalyst which accumulates on the bottom of (D) is continuously removed and pneumatically conveyed, through line (T1) and with the introduction of carrier gas, for example, air or nitrogen, to the upper part of the regenerator (R). The stream of air (21), taken from the atmosphere (19), compressed in (K2) to give stream (20) and which is preheated in (G2), is fed to the regenerator. The air (21), fed to the base by means of a suitable distributor, not illustrated in the figure, burns the carbonaceous deposits (coke) deposited on the surface of the catalyst and, rising in countercurrent, keeps the solid in fluidized state. The effluent gases (22) from the regenerator are cooled in (G2), filtered in (F) and discharged from (ST).

Analogously, the regenerated catalyst, which accumulates on the bottom of (R), is continuously removed and pneumatically conveyed, through line (T2), using ethane (6) as carrier gas, to the upper part of the dehydrogenation reactor (D). During the transfer phase, the ethane is thoroughly mixed with the hot catalyst and is partially transformed to ethylene, lowering the temperature of the catalyst to values compatible with the dehydrogenation of ethylbenzene.

The dehydrogenated product (8), which essentially consists of styrene, ethylene, non-converted ethylbenzene and ethane, methane, hydrogen and other products, such as toluene and benzene, is cooled in (G1), washed from the entrained powders in (S), further cooled in the condenser (C) and fed to the separator (V). A stream (12) of condensable products, essentially consisting of styrene, ethylbenzene and other by-products (benzene, toluene) is recovered from the bottom of (V) whereas a stream (11) of light products essentially consisting of ethylene, ethane, methane and hydrogen is recovered at the head.

The stream (12) goes to the distillation unit (S), for example a unit comprising one or more distillation columns, from which high purity (>99.5%) styrene (18) is recovered together with ethylbenzene (16), recycled to the dehydrogenation, and by-products (17) which are sent for subsequent treatment.

The stream (11) is brought to the operating pressure of the alkylation unit in (K1), separated from the hydrogen (15) in the membrane removal system (LT) and recycled to (A), as primary feed, by means of line (14).

An illustrative but non-limiting example is provided hereunder for a better understanding of the present invention and for its embodiment.

EXAMPLE

An integrated plant is described, for the production of styrene, which operates for 8,400 hours/year with a normal yearly production of 3,500 tons of styrene.

A contemporaneous dehydrogenation of ethane and ethylbenzene is effected analogously to the procedure described in U.S. Pat. No. 6,031,143. The ethylbenzene necessary for the production of styrene is premixed with ethane so that the feeding to the reactor consists of 30% molar of ethylbenzene and 70% molar of ethane. The reaction is carried out at an average pressure in the fluid bed of 1.5 atmospheres and at a temperature ranging from 550° C. at the bottom of the reactor to 600° C. at the upper end of the catalytic bed, where the hot regenerated catalyst coming from the reactor, is fed. The space velocity (GHSV) is 300 Nl/h of gas per liter of catalyst. The dehydrogenation catalyst comprises gallium oxide (2.33% by weight), potassium oxide (0.6% by weight), platinum (75 ppm), silica (1.56% by weight), the complement to 100 being alumina, and the residence time of the solid in the reactor is equal to 12 minutes. The ethylbenzene conversion is 52% by weight and the selectivity to styrene 92% by weight. The ethane conversion is 10% by weight and the selectivity to ethylene 90% by weight. In this way, the molar ratio between reacted ethylbenzene and ethylene produced is equal to 2.5.

Another amount of ethane, equal to 60% of the quantity premixed with ethylbenzene, is fed to the base of the carrier line which brings the regenerated catalyst to an average temperature of 650° C. and to an average pressure of 2 bars from the regenerator to the reactor.

The ethane acts as carrier gas but also partly reacts to form ethylene. The yield to ethylene is 20% by weight, and consequently, after the effluent gas from the fluid bed of the reactor is mixed with the carrier gas from the regenerator to the reactor, the molar ratio between reacted ethylbenzene and ethylene formed is equal to 0.99. A quantity of ethylene was therefore produced, by the dehydrogenation of ethane, which was sufficient to be used as reagent in the alkylation section and produce all the ethylbenzene which reacts in the dehydrogenation reactor.

The invention claimed is:

1. An integrated process for the production of alkyl and alkenyl substituted aromatic compounds which comprises:
    a) feeding to an alkylation unit, a stream consisting of a $C_6$–$C_{12}$ aromatic hydrocarbon and a recycled stream containing a $C_2$–$C_5$ alkenyl hydrocarbon;
    b) optionally mixing the stream leaving the alkylation unit, containing the alkylaromatic compound, with a stream consisting of a $C_2$–$C_5$ alkyl hydrocarbon;
    c) feeding the stream of step (b) to a fluid bed dehydrogenation/regeneration unit containing a catalyst capable of dehydrogenating, also simultaneously, the alkyl hydrocarbon, optionally present, and the alkylaromatic compound;
    d) continuously discharging the exhausted catalyst which accumulates on the bottom of the dehydrogenation reactor and feeding it to the head of the regeneration reactor;
    e) continuously discharging the regenerated catalyst which accumulates on the bottom of the regeneration reactor and feeding it to the head of the dehydrogenation reactor;
    f) feeding the hydrocarbon stream leaving the dehydrogenation reactor to a separation section to produce a stream essentially consisting of the alkenyl substituted aromatic compound and a stream containing the alkenyl hydrocarbon;
    g) recycling the stream containing the alkenyl hydrocarbon to the alkylation unit;
    said integrated process being characterized in that the fluid for transporting the catalyst, which is deposited on the bottom of the regenerator at a temperature of 650–800° C., to the dehydrogenation reactor consists of a $C_2$–$C_5$ alkylhydrocarbon.

2. The integrated process according to claim 1, wherein the $C_6$–$C_{12}$ aromatic hydrocarbon is benzene.

3. The integrated process according to claim 1, wherein the $C_2$–$C_5$ alkyl/alkenyl hydrocarbon is ethane/ethylene.

4. The integrated process according to claim 1, wherein the recycled stream consists of 20–95% in moles of ethane and 5–80% in moles of ethylene, respectively.

5. The integrated process according to claim 1, wherein the streams are fed to the alkylation unit so as to have molar ratios benzene/ethylene ranging from 1.8 to 50.

6. The integrated process according to claim 1, wherein the alkylation unit comprises a catalytic distillation reactor which operates in mixed gas-liquid phase.

7. The integrated process according to claim 1, wherein the alkylation unit comprises a continuous fixed bed reactor functioning in gas phase.

8. The integrated process according to claim 6, wherein the alkylation catalyst is selected from synthetic and natural porous crystalline solids wherein the atomic ratio of silicon/aluminum ranges from 5/1 to 200/1.

9. The integrated process according to claim 8, wherein the alkylation catalyst is selected from the group consisting of Y zeolites, beta zeolites, mordenite zeolites, omega zeolites, A zeolites, X zeolites, L zeolites, porous crystalline solid MCM-22, porous crystalline solid MCM-36, porous crystalline solid MCM-49, porous crystalline solid MCM 56 and porous crystalline solid ERS-10.

10. The integrated process according to claim 7, wherein the alkylation catalyst is selected from zeolites of the ZSM group in which the atomic ratio silicon/aluminum ranges from 20/1 to 200/1.

11. The integrated process according to claim 10, wherein the alkylation catalyst is selected from ZSM-5, ZSM-11, ZSM-12, ZSM-23, ZSM-35, ZSM-38 and ZSM-48 zeolites.

12. The integrated process according to claim 11, wherein the alkylation catalyst is ZSM-5.

13. The integrated process according to claim 1, wherein the alkylation reaction is carried out at a temperature ranging from 50 to 450° C.

14. The integrated process according to claim 6, wherein the alkylation temperature, varying along the catalytic bed, ranges from 140 to 350° C.

15. The integrated process according to claim 7, wherein the alkylation temperature ranges from 325 to 450° C.

16. The integrated process according to claim 1, wherein the pressure inside the alkylation reactor is maintained at values ranging from 0.5 to 6 MPa.

17. The integrated process according to claim 1, wherein the alkylation unit comprises a separation system to respectively obtain a substantially pure stream of non-converted aromatic hydrocarbon, a substantially pure stream of alkyl substituted aromatic compound, and a stream of heavier products essentially consisting of di- or polyalkyl substituted aromatic compounds.

18. The integrated process according to claim 17, wherein the separation system consists of a series of distillation columns, from the first of which non-converted aromatic hydrocarbon is recovered and recycled to the alkylation reactor or to a transalkylation unit, alkyl substituted aromatic compound is recovered from the second distillation column and fed to the dehydrogenation unit, and polyalkyl substituted aromatic compounds are recovered from the third column.

19. The integrated process according to claim 18, wherein the polyalkyl substituted aromatic compounds are fed to the transalkylation unit for transalkylation with $C_6$–$C_{12}$ aromatic hydrocarbons to produce corresponding alkyl substituted aromatic compounds.

20. The integrated process according to claim 19, wherein the transalkylation is carried out in a fixed bed reactor functioning in liquid phase in which a transalkylation catalyst selected from the group consisting of Y zeolite, beta zeolite and mordenite, is present.

21. The integrated process according to claim 19, wherein, in the case of the transalkylation of polyethylbenzenes with benzene, the molar ratio benzene/ethylene calculated with respect to the total moles of benzene present as such and as polyethylene and on the total moles of ethylene present as substituent in the polyethylbenzenes, ranges from 1.8/1 to 17/1.

22. The integrated process according to claim 21, wherein the temperature in the transalkylation reactor is maintained at 50 to 300° C. whereas the pressure is maintained at 0.02 to 5.5 MPa.

23. The integrated process according to claim 1, wherein the $C_2$–$C_5$ alkyl hydrocarbon fed to the stream leaving the alkylation unit is equal to 0–70% by weight of the total.

24. The integrated process according to claim 1, wherein the stream containing the alkylation product is fed in gas phase to the base of the dehydrogenation reactor operating at a temperature ranging from 450 to 650° C. and at a pressure ranging from 0.1 to 3 ata.

25. The integrated process according to claim 1, wherein the regeneration reactor is fed with preheated air and optionally with fuel gas to supply heat by its combustion.

26. The integrated process according to claim 1, wherein the temperature profile inside the regeneration reactor generally ranges from 600 to 800° C.

27. The integrated process according to claim 1, wherein the regenerated catalyst is continuously removed from the bottom of the regeneration reactor and is fed to the dehydrogenation reactor using the $C_2$–$C_5$ alkyl hydrocarbon as carrier fluid in a quantity ranging from 30 to 100% by weight with respect to the total weight used.

28. The integrated process according to claim 1, wherein the dehydrogenation catalyst is based on iron and one or more promoters, selected from alkaline or earth-alkaline metals and lanthanides, on alumina in delta or theta phase or in a mixture of delta+theta, theta+alpha or delta+theta+alpha phases, modified with silica, and having a surface area of preferably less than 150 m²/g, determined with the BET method.

29. The integrated process according to claim 28, wherein the dehydrogenation catalyst comprises:
  1–60% by weight, of iron oxide;
  0.1–20% by weight of at least one alkaline or earth alkaline metal oxide;
  0–15% by weight of a second promoter selected from lanthanide oxides;
  the complement to 100 being alumina modified with 0.08–5% by weight of silica.

30. The integrated process according to claim 1, wherein the dehydrogenation catalyst is selected from those based on gallium and platinum or based on chromium and tin.

31. The integrated process according to claim 30, wherein the catalyst based on gallium and platinum comprises:
  0.1–34% by weight of $Ga_2O_3$;
  1–99 ppm (by weight) of platinum;
  0.05%–5% by weight of an alkaline and/or earth alkaline oxide;
  0.08–3% by weight of silica;
  the complement to 100 being alumina in delta or theta phase or in a mixture of delta+theta, theta+alpha or delta+theta+alpha phases with a surface area of less than 150 m²/g, determined with the BET method.

32. The integrated process according to claim 30, wherein the catalyst based on chromium and tin comprises:
- 6–30% by weight of $Cr_2O_3$;
- 0.1–3.5% by weight of SnO;
- 0.4%–3% by weight of an alkaline oxide;
- 0.08–3% by weight of silica;
- the complement to 100 being alumina in delta or theta phase or in a mixture of delta+theta, theta+alpha or delta+theta+alpha phases with a surface area of less than 150 $m^2/g$, determined with the BET method.

33. The integrated process according to claim 1, wherein, at the end of the dehydrogenation, a dehydrogenated stream is recovered, which comprises 15–30% by weight of styrene; 7–15% by weight of ethylene; 10–50% by weight of non-reacted ethylbenzene and 15–55% by weight of non-reacted ethane.

34. An integrated process for the production of alkyl and alkenyl substituted aromatic compounds which comprises:
- a) feeding to an alkylation unit, a stream consisting of a $C_6$–$C_{12}$ aromatic hydrocarbon and a recycled stream containing a $C_2$–$C_5$ alkenyl hydrocarbon;
- b) optionally mixing the stream leaving the alkylation unit, containing the alkylaromatic compound, with a stream consisting of a $C_2$–$C_5$ alkyl hydrocarbon;
- c) feeding the stream of step (b) to a fluid bed dehydrogenation/regeneration unit containing a catalyst capable of dehydrogenating, also simultaneously, the alkyl hydrocarbon, optionally present, and the alkylaromatic compound;
- d) continuously discharging the exhausted catalyst which accumulates on the bottom of the dehydrogenation reactor and feeding it to the head of the regeneration reactor;
- e) continuously discharging the regenerated catalyst which accumulates on the bottom of the regeneration reactor and feeding it to the head of the dehydrogenation reactor;
- f) feeding the hydrocarbon stream leaving the dehydrogenation reactor to a separation section to produce a stream essentially consisting of the alkenyl substituted aromatic compound and a stream containing the alkenyl hydrocarbon;
- g) recycling the stream containing the alkenyl hydrocarbon to the alkylation unit;
- said integrated process being characterized in that the fluid for transporting the catalyst, which is deposited on the bottom of the regenerator at a temperature of 650–800° C., to the dehydrogenation reactor, consists of a $C_2$–$C_5$ alkyl hydrocarbon and that the dehydrogenation reactor is a riser reactor in equicurrent, in which the solid is completely carried upwards pneumatically by a gas.

35. The integrated process according to claim 34, wherein the space velocity of the gas (GHSV) is greater than 500 $h^{-1}$.

36. The integrated process according to claim 34, wherein the alkyl hydrocarbon is fed to the bottom of the riser, entering into contact with the catalyst at the maximum reaction temperature, whereas the stream containing the alkylaromatic compound is fed at an intermediate height of the riser where the temperature has dropped to compatible levels for the corresponding dehydrogenation.

* * * * *